United States Patent
Skoglund (10) Patent No.: US 9,753,454 B2
(45) Date of Patent: Sep. 5, 2017

(54) METHOD AND AN APPARATUS FOR DETECTING A TRANSITION FROM A FIRST PHASE TO A SECOND PHASE

(71) Applicant: TETRA LAVAL HOLDINGS & FINANCE S.A., Pully (CH)

(72) Inventor: Tomas Skoglund, Lund (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 100 days.

(21) Appl. No.: 14/429,076

(22) PCT Filed: Sep. 13, 2013

(86) PCT No.: PCT/EP2013/068964
§ 371 (c)(1),
(2) Date: Mar. 18, 2015

(87) PCT Pub. No.: WO2014/044600
PCT Pub. Date: Mar. 27, 2014

(65) Prior Publication Data
US 2015/0248130 A1    Sep. 3, 2015

(30) Foreign Application Priority Data
Sep. 18, 2012 (SE) .................................. 1251047

(51) Int. Cl.
*G05B 23/02* (2006.01)
*G05B 11/16* (2006.01)
*G01N 33/14* (2006.01)

(52) U.S. Cl.
CPC ......... *G05B 23/0218* (2013.01); *G01N 33/14* (2013.01); *G05B 11/16* (2013.01)

(58) Field of Classification Search
CPC ..... G01N 33/14; G05B 11/16; G05B 23/0218
(Continued)

(56) References Cited

U.S. PATENT DOCUMENTS 5,576,495 A    11/1996    Vetterick
6,799,883 B1 *    10/2004    Urquhart ........... B01F 15/00227
                                                                        137/3

(Continued)

FOREIGN PATENT DOCUMENTS

GB    2 057 141 A    3/1981
WO    WO 2004/097346 A    11/2004

OTHER PUBLICATIONS

International Search Report (PCT/ISA/210) mailed on Dec. 13, 2013, by the European Patent Office as the International Searching Authority for International Application No. PCT/EP2013/068964.

*Primary Examiner* — Hezron E Williams
*Assistant Examiner* — Marrit Eyassu
(74) *Attorney, Agent, or Firm* — Buchanan Ingersoll & Rooney PC (57) ABSTRACT

It is provided an apparatus for detecting a transition from a first phase to a second phase in a processing line. The apparatus comprises a first sensor for gathering data indicating product concentration, a second sensor for gathering data indicating product concentration. The first sensor is placed upstream of the second sensor. Further, the apparatus comprises a control device configured to receive a first data set from the first sensor and a second data set from the second sensor, and to calibrate the second sensor by comparing the second data set with the first data set.

4 Claims, 5 Drawing Sheets

(58) Field of Classification Search
USPC .......................................................... 73/61.43
See application file for complete search history.

(56) References Cited

U.S. PATENT DOCUMENTS

| | | | |
|---|---|---|---|
| 6,881,381 B1* | 4/2005 | Asher | C10L 1/14 |
| | | | 250/339.09 |
| 7,363,800 B2* | 4/2008 | Gysling | G01F 1/74 |
| | | | 702/23 |
| 2001/0035198 A1* | 11/2001 | Carawan | A23C 3/033 |
| | | | 134/18 |
| 2002/0088823 A1* | 7/2002 | Tabacchi | B67D 1/1206 |
| | | | 222/52 |
| 2004/0074312 A1* | 4/2004 | Gysling | G01F 1/668 |
| | | | 73/861.04 |
| 2005/0109078 A1* | 5/2005 | Chen | G01N 7/14 |
| | | | 73/23.29 |
| 2007/0033988 A1 | 2/2007 | Skoglund | |
| 2009/0151419 A1* | 6/2009 | Doniat | G01N 27/06 |
| | | | 73/1.03 |

\* cited by examiner

METHOD AND AN APPARATUS FOR DETECTING A TRANSITION FROM A FIRST PHASE TO A SECOND PHASE

TECHNICAL FIELD

The invention generally relates to the field of processing systems. More particularly, the invention relates to a method for detecting a transition from a first phase to a second phase.

BACKGROUND OF THE INVENTION

Today, food processing plant owners around the world are striving to improve the performance of their equipment. One reason for this is that the price for food has increased significantly in several areas, making it more important to reduce the product loss. Another reason is that the demands for environmental friendly food processing are higher making it more important to, for instance, reduce the usage of water.

Product losses and water consumption for a food processing system are generally high in connection to or during cleaning of the system and changing from one product to another. The reason for this is that when the processing of the product is stopped the system will still contain remaining product. In order to capture the remaining product it is a common approach to flush the system with clean water. A mix phase, that is, a mix of the remaining product and the clean water, is then fed through a product recovery system in order to capture product residues and feeding them back into the system. When the product concentration is below a certain threshold the process of recovering product residues is stopped and the cleaning process is started, which most often comprise adding different cleaning agents in order to make sure that all kind of residues are removed.

As can be readily understood, in order to reduce product losses and the usage of water the mix phase should be as distinct as possible. In other words, the mix phase, i.e. transition from only product, also referred to as product phase, to only clean water, also referred to as water phase, should be as short as possible. Different technologies for achieving this have been developed. One example is the so-called "ice pigging" technology in which an ice and water mixture is added in order to make a distinct differentiator between the product phase and the water phase. Another example is to add a rubber object in order to keep the product phase and the water phase apart.

Further, in some cases, a product phase is followed by another product phase. In such cases it is also important to keep the mix phase, in this situation comprising a mix of the first product and the second product, short in order to be able to reduce the product loss.

Even though there are technologies for keeping two phases apart, there is a need to optimize the process further in order to be able to reduce water usage and product losses.

SUMMARY

Accordingly, the present invention preferably seeks to mitigate, alleviate or eliminate one or more of the above-identified deficiencies in the art and disadvantages singly or in any combination and solves at least the above mentioned problems e.g. by providing means for detecting a transition from a first phase to a second phase in a processing line.

According to a first aspect an apparatus for detecting a transition from a first phase to a second phase in a processing line is provided. The apparatus comprising a first sensor for gathering data indicating product concentration, a second sensor for gathering data indicating product concentration, wherein said first sensor is placed upstream said second sensor, and a control device configured to receive a first data set from said first sensor and a second data set from said second sensor, and to calibrate said second sensor by comparing said second data set with said first data set.

The wording "phase" can be explained as what is currently flowing in the processing system. For instance, when a first product is being treated the system can be said to be in first product phase. Similarly, when a mixture of water and the first product is flowing through the system it is said to be in a mix phase, more specifically a first product and water mix phase.

The apparatus may further comprise a state tracker for keeping track of a first sensor state and a second sensor state, wherein said first data set and said second data set received by said control device is captured when said first sensor and said second sensor are in corresponding sensor states.

Further, the first sensor state may be selected from a first group comprising first phase at first sensor (P11) and second phase at first sensor (P21), and said second sensor state may be selected from a second group comprising first product at second sensor (P12) and second product at second sensor (P22), wherein said first phase at first sensor (P11) and said first phase at second sensor (P12) are corresponding sensor states, and said second phase at said first sensor (P21) and said second phase at said second sensor (P22) are corresponding states.

The first group may further comprise water at first sensor (W1), and said second group may further comprise water at second sensor (W2), wherein said water at first sensor (W1) and said water at second sensor (W2) are corresponding states.

Processing equipment, such as heat treatment equipment, homogenizers, separators, may be placed downstream said first sensor and upstream said second sensor.

The first sensor and/or the second sensor may be sensors of a type measuring turbidity and/or conductivity.

The control device may be configured to indicate that said transition from said first phase to said second phase has occurred when detecting a product concentration change using said first sensor followed by a subsequent product concentration change using said second sensor.

The product concentration change may be greater than said subsequent product concentration change.

The product concentration change may be a product concentration drop, i.e. less product being present.

According to a second aspect it is provided a system comprising a processing line provided with an apparatus according to the first aspect.

The system may further comprise a conduit for feeding a marker fluid into said processing line.

The marker liquid may be water.

According to a third aspect it is provided a kit of parts configured to be applied on a processing line such that a transition from a first phase to a second phase in a processing line can be detected, said kit of parts comprising a first sensor for gathering data indicating product concentration, a second sensor for gathering data indicating product concentration, wherein said first sensor is arranged to be placed upstream said second sensor, and a control device configured to receive a first data set from said first sensor and a second data set from said second sensor, and to calibrate said second sensor by comparing said second data set with said first data set.

According to a fourth aspect it is provided a method for detecting a transition from a first phase to a second phase in a processing line, said method comprising receiving a first data set indicating product concentration from a first sensor, receiving a second data set indicating product concentration from a second sensor, wherein said second sensor is placed downstream said first sensor, calibrating said second sensor by comparing said second data set with said first data set.

The method may further comprise determining a first sensor state and a second sensor state, wherein said first data set and said second data set received by said control device are captured when said first sensor and said second sensor are in corresponding sensor states.

The method may further comprise indicating said transition from said first phase to said second phase when detecting a product concentration change using said first sensor followed by a subsequent product concentration change using said second sensor.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, wherein.

DETAILED DESCRIPTION OF PREFERRED EMBODIMENTS

Figure 1:
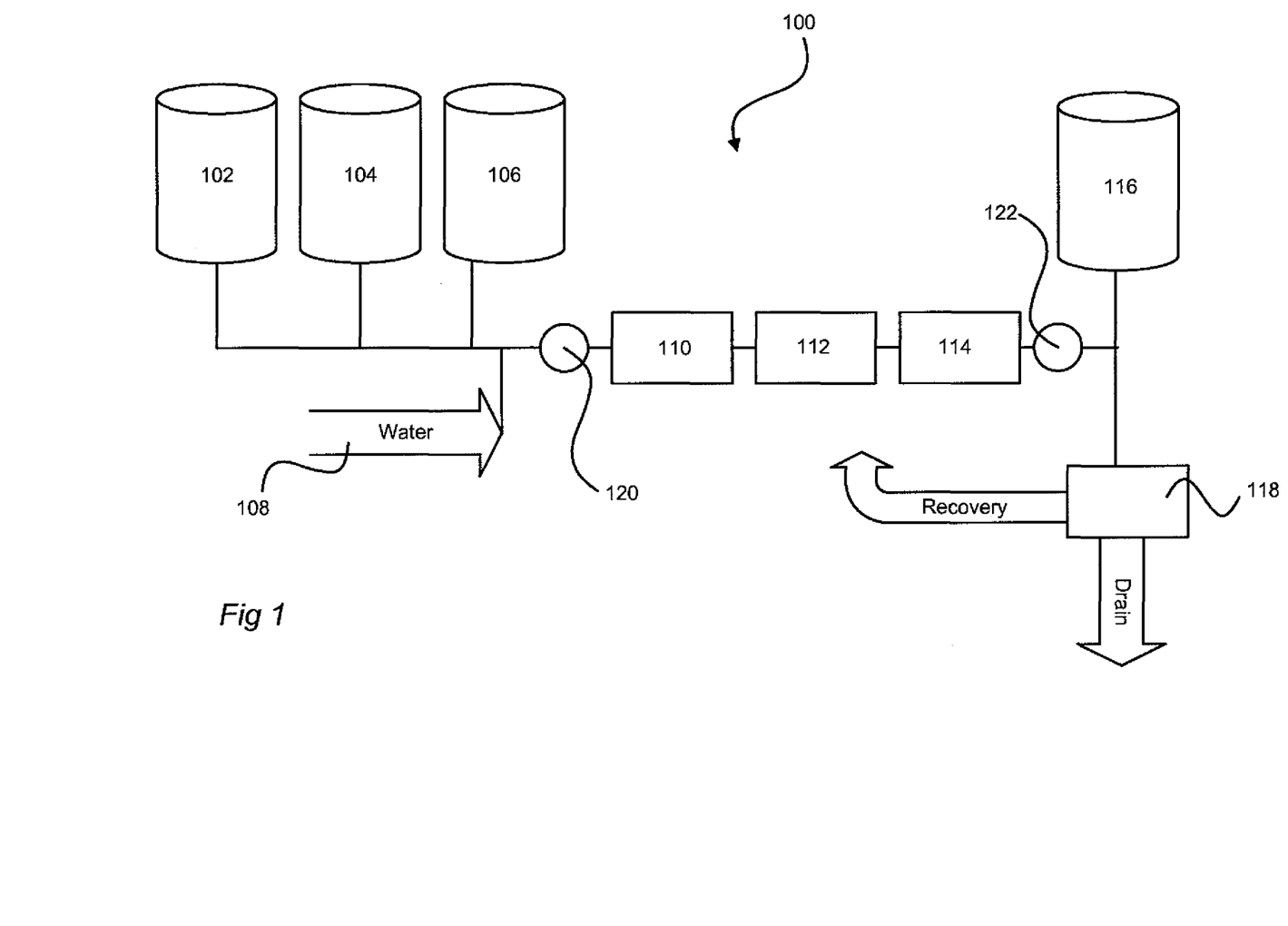
FIG. 1 generally illustrates an example of a processing system.

FIG. 1 generally illustrates an example of a processing system 100. In this particular example, three storage tanks—a first tank 102, a second tank 104 and a third tank 106—are used for storing different products. Further, a conduit 108 for water can be used for flushing the processing system 100.

Three pieces of processing equipment—a first processing device 110, a second processing device 112 and a third processing device 114—can be used for treating any of the different products. After being treated the products can be stored in a fourth storage tank 116.

When cleaning the system 100, it is a common approach to first flush the system with clean water in order to filter out product residues left in the system 100 and feed these residues back into the system via recovery system 118 in order to reduce product losses. This process may also be referred to as reclaiming. When a product concentration is below a certain threshold and it hence does not make anymore economic sense to filter out product residues, a mix phase comprising the product residues and the clean water is sent to the drain or alternatively to a further system (not illustrated) for recovering product residues for e.g. using them for pigs' feed.

In a second step of the cleaning process a mix of water and detergents are sent through the system 100, and finally, in a third step, before starting product treatment again, clean water is flushed through the system in order to remove the cleaning agents left in the system 100.

For some products, like milk and chocolate milk, the system 100 does not need to be cleaned when switching from one product to the other. In the example with milk and chocolate milk, the only effect of not cleaning the system between the two different products will be a somewhat higher concentration of milk in the first liters of produced chocolate milk.

For some other products, like two different juices—a first juice product and a second juice product, it may be more critical to make sure that the first juice product being treated in the system is not affecting the flavour of the second juice product being treated by the same system. In some cases, it may be sufficient to use a water plug in order remove product residues from the first juice product and thereby avoiding that the flavour of the second juice product is affected. Therefore, in order to reduce the usage of water and cleaning agents, cleaning can be avoided in some situations when switching from one product to another.

However, on a general basis, the inventor has realized that in order to be able to minimize product losses and water usage it is beneficial to be able to detect a transition from one phase to another, e.g. to detect when going from processing a first product to handling a mix of the first product and water. An advantage of having the information about what phase that is being processed is that instead of using pre-set conditions, such as time parameters, for when to e.g. send output to the recovery system 118 or the intermediate storage tank 116 this may be controlled by real time measurements and hence not requiring the same safety margins. This implies in turn less product losses, less water usage and higher uptime for production. Therefore, in order reduce product losses and water usage an apparatus for detecting a transition from a first phase to a second phase can be used. Such an apparatus can comprise a first sensor 120 and a second sensor 122.

Figure 2:
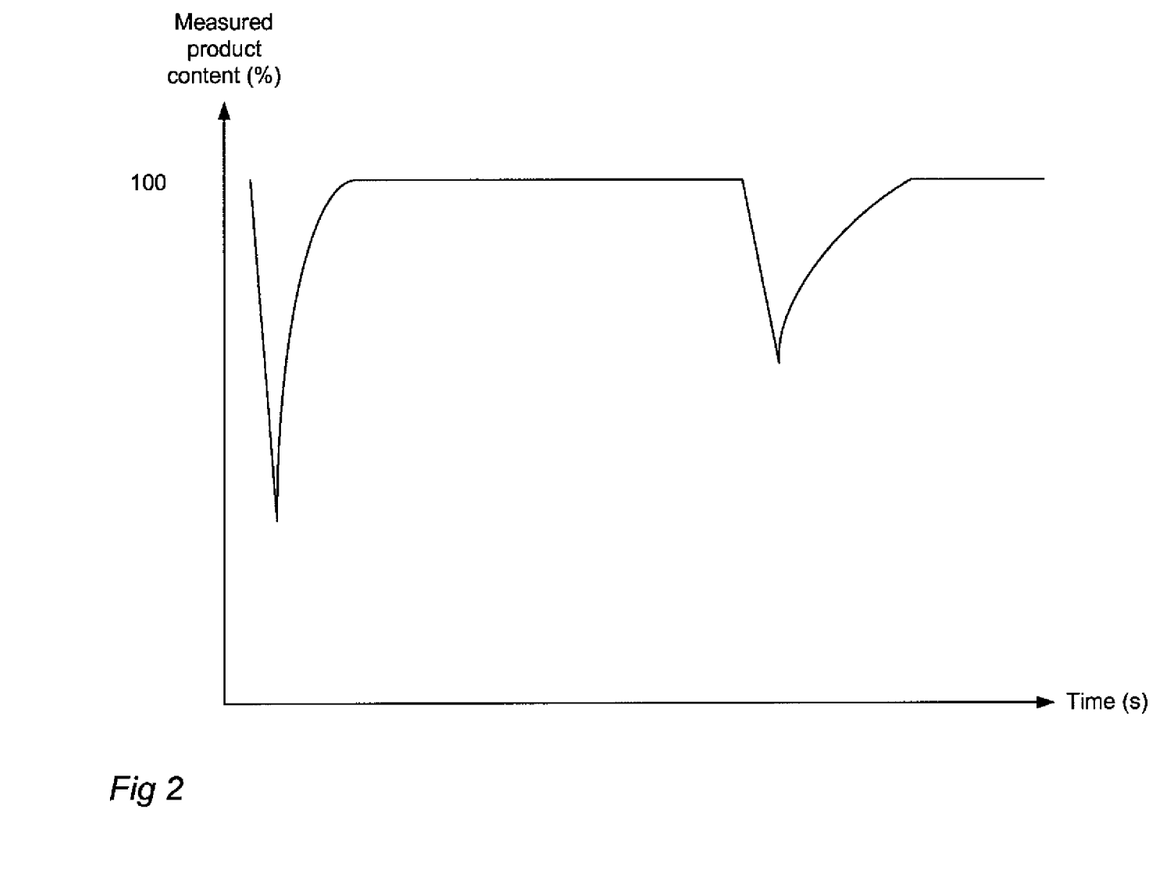
FIG. 2 illustrates an example of measured product content over time for a processing line.

The first sensor 120 can be placed upstream said second sensor 122. An effect of this is for instance that if water is flushed through the system after treating the first juice product and before treating the second juice product a product concentration drop can be first measured by the first sensor 120 and later by the second sensor 122, as illustrated in FIG. 2. Due to that the second sensor 122 is placed downstream in the processing system the concentration drop measured by the second sensor 122 will be diluted and hence having a lower magnitude than the concentration drop measured by the first sensor 120. By taking this into account it is possible to detect the switch from the first product to the second product in a reliable manner.

The first sensor 120 and the second sensor 122 may be of the same type, e.g. turbidity sensors, conductivity sensors or a combination thereof. An advantage of having the two sensors of the same type is that one of them may be used for calibrating the other one. Further, using the same type of sensors has the advantage that they will provide the same signal for same media.

An advantage of having two sensors compared to only having a single sensor is that since the first sensor 120 is calibrating the second sensor 122 there is no need for any absolute value as is the case for the single sensor solution.

Still an advantage is that an automatic calibration can be made for different product recipes since the first sensor 120 is calibrating the second sensor 122.

An even further advantage is that a better self diagnosis can be achieved. For instance, if the signals from the first sensor 120 and the second sensor 122 are detected to significantly differ a notification can be sent to an operator to investigate the sensors.

Further, since the first sensor 120 is calibrating the second sensor 122 less time is needed during commission of a processing line.

Figure 3:
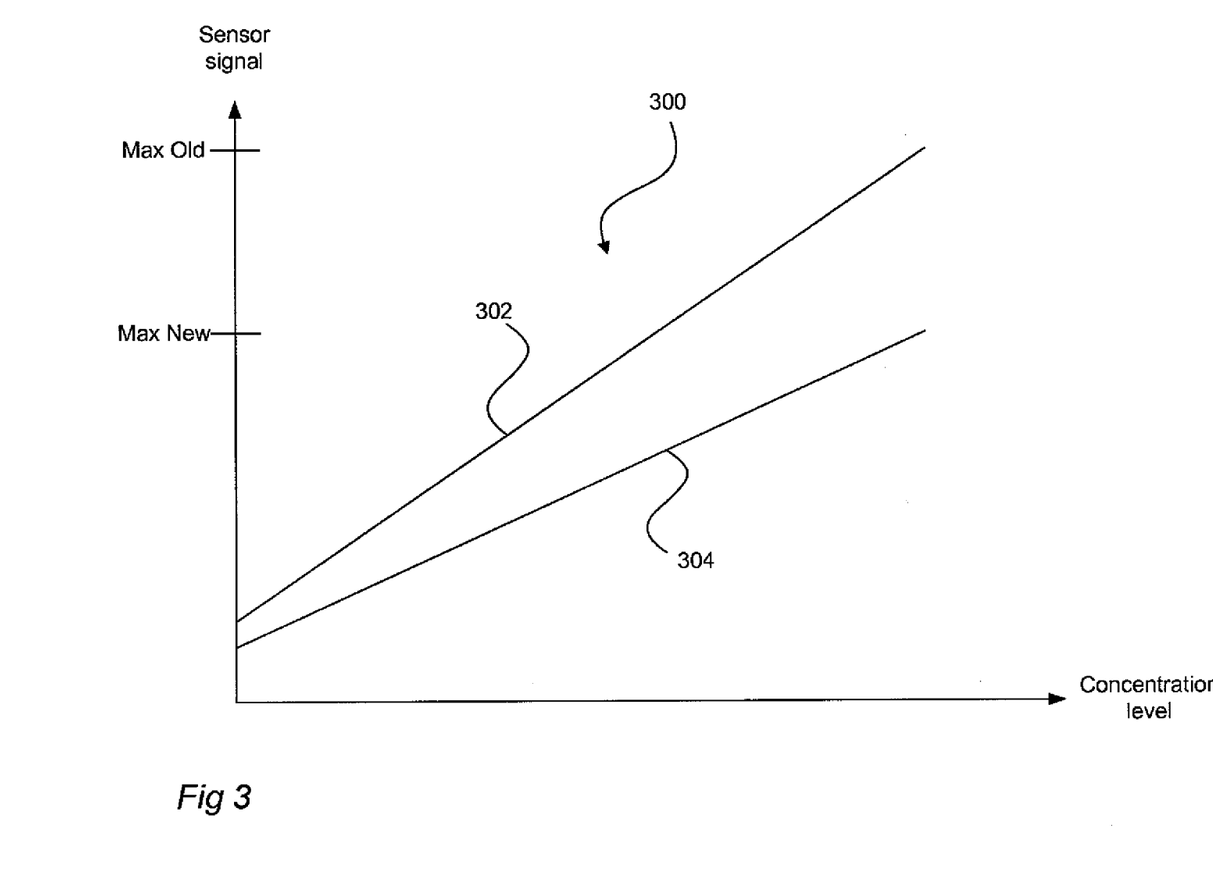
FIG. 3 illustrates an example of how sensor signal output may drift over time due to wear.

FIG. 3 illustrates an example diagram 300 with a first curve 302 showing the relationship between sensor signal and concentration level at a certain point of time for the first sensor 120 or the second sensor 122, and a second curve 304 showing the same relationship but a later point in time when the sensors have started to drift due to that they are worn. As illustrated, as time passes the relationship between sensor signal and concentration level is affected.

By having two sensors, one of them may be used as a reference for calibrating the other. In the example illustrated in FIG. 1, the first sensor 120 can be used for calibrating the second sensor 122. One reason for having the first sensor 120 as a reference is that this sensor is placed at an early stage in the processing system 100, e.g. just after the storage tanks 102, 104, 106 as illustrated in FIG. 1, and thus that there is less time for diluting a difference between two phases implying that the concentration level can be estimated with a higher certainty compared to the second sensor 122 placed farther away from the storage tanks 102, 104, 106.

Further, as illustrated in FIG. 3, a maximum sensor signal may be changed over time, herein referred to as MaxOld and MaxNew. In the same way the minimum sensor signal can be changed over time. Herein changing an interval over time in this way is referred to as dynamic settings.

Figure 4:
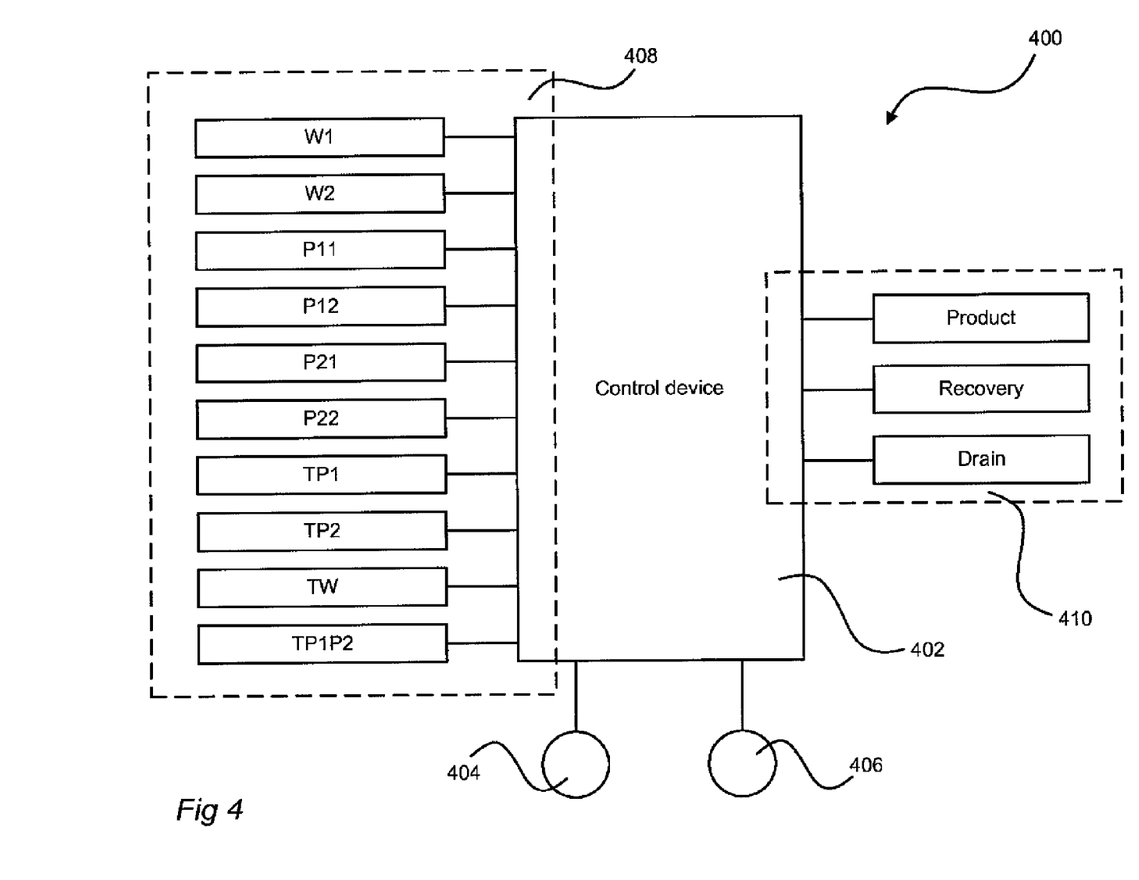
FIG. 4 generally illustrates an example of a control arrangement.

Referring to FIG. 4, an example of a control arrangement 400 is generally illustrated. The wording control arrangement should in this context be given a broad interpretation as an arrangement comprising equipment for process control. As will be understood by a skilled person, different kind of equipment can be used and combined for reducing the suggested principle into practice. Further, it will also be understood by the skilled person that the operations described may take place in different pieces of equipment.

A control device 402, e.g. a computer, a microcontroller, a PLC (Programmable Logic Controller) or any other device with inputs and outputs and data processing capabilities, can be provided with a first sensor input 404 and a second sensor input 406 for receiving data from the first sensor 120 and the second sensor 122, respectively. Further, a state tracker 408 can be provided for determining a first sensor state and a second sensor state, and a control output handler 410 for outputting information to a control system of the processing system 100.

The state tracker 408 can receive information about the first sensor state and the second sensor state from the control system of the processing system 100, or alternatively the control device 402 itself can determine the first sensor state and the second sensor state based on information received from the control system of the processing system, such as flow velocity, valve settings, etc.

In the example illustrated the first sensor state can be water at first sensor (W1), first product at first sensor (P11) and second product at second sensor (P21). The second sensor state can be water at second sensor (W2), first product at second sensor (P12), second product at second sensor (P22), transition wait for first product at second sensor (TP1), transition wait for second product at second sensor (TP2), transition wait for water at second sensor (TW) and transition wait for first or second product at second sensor (TP1P2). Further, if more than two products are treated in the system, additional states may be added taken into account the extra states the first sensor and the second sensor may be in.

When the first sensor state is water at first sensor (W1) and the second sensor state is water at second sensor (W2) a minimum level of the sensor signal can be calibrated.

When the first sensor state is first product at first sensor (P11) and the second sensor state is first product at second sensor (P12) a sensor signal for the first product can be calibrated.

Similarly, when the first sensor state is second product at first sensor (P21) and the second sensor state is second product at second sensor (P22) a sensor signal for the second product can be calibrated.

In order to determine the output to the control system for the processing system two threshold values can be used—good product threshold (GPT) and reclaim product threshold (RPT). When a sensor signal (QT2) for the second sensor 122 is above the GPT the system will be set to treat the product according to normal production mode, which in the example illustrated in FIG. 1 can imply that the product is transferred to the fourth storage tank 116 via the processing devices 110, 112, 114. When the sensor signal for the second sensor 122 is below the GPT, but above the RPT, the product will be transferred through a product recovery system in order to capture product residues and feed them back into the system. Further, when the sensor signal is below the RPT the product will be transferred to the drain.

Figure 5:
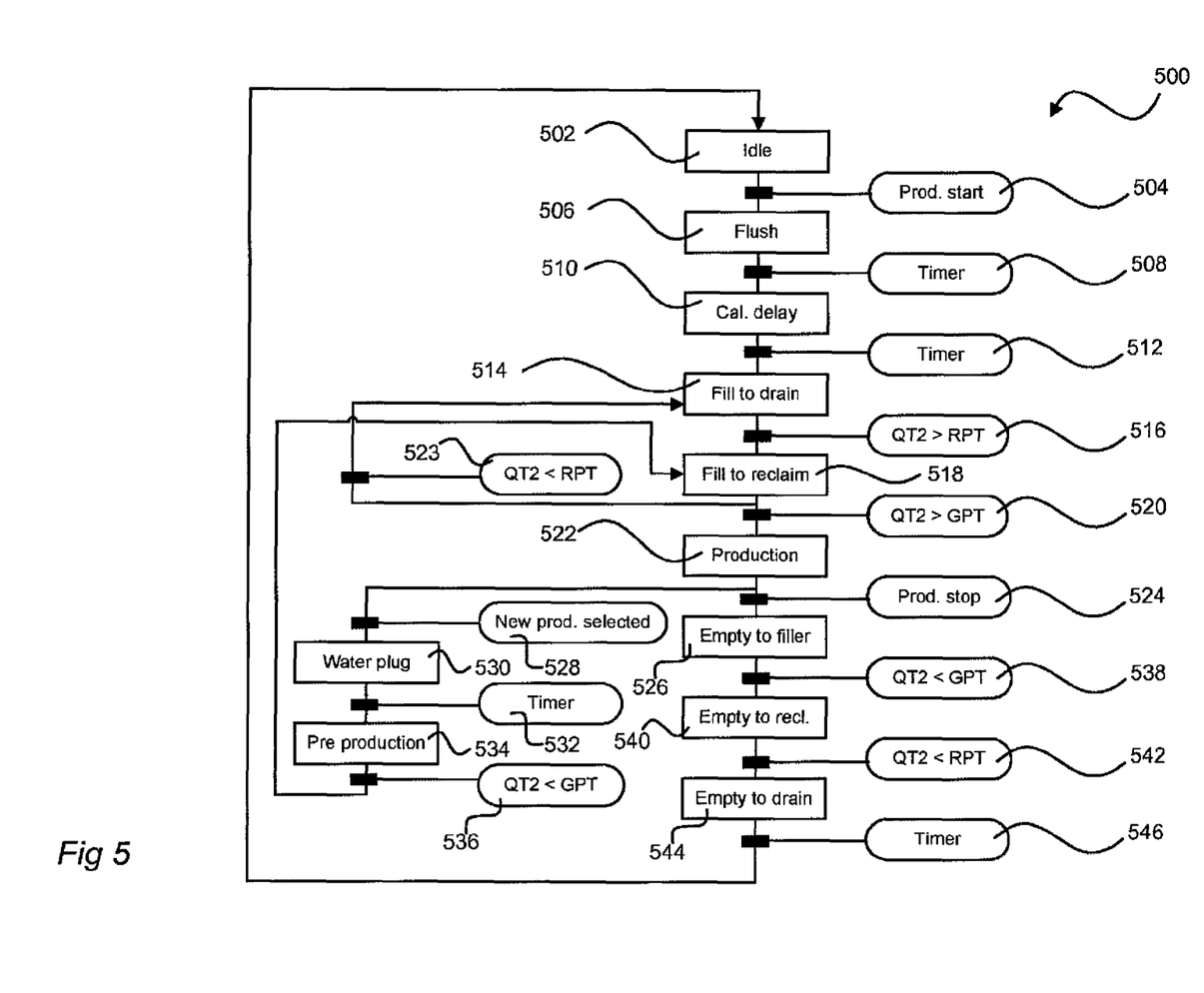
FIG. 5 generally illustrates an example of a running scheme.

FIG. 5 illustrates an example of a scheme 500 for running the processing system 100.

Before starting the processing system 100, a mode can be set to idle mode 502. After having received a production start input 504, the mode can be changed to flush mode 506. In flush mode, clean water is run through the system 100, or in some situations only part of the system, in order to make sure e.g. that food safety can be assured.

Next, after having flushed the system for a period of time, e.g. indicated by receiving a timer lapse input 508, the mode of the processing system 100 is changed to calibration delay mode 510 in which the second sensor 122 is calibrated by using the first sensor 120 as explained above.

After a period of time, e.g. indicated by receiving a timer lapse input 512, a fill to drain mode 514 is entered. In this mode the processing system 100 is set to deliver to the drain.

When a QT2 above RPT input 516 is received, i.e. when it makes sense to filter out product residues, a fill to reclaim mode 518 is entered. In this mode the processing system 100 is delivering to a product recovery system in order to capture the product residues and feed them back into the processing system.

After receiving a QT2 above GPT input 520 may enter a production mode 522.

In production mode 522, the processing system 100 can either by receiving a production stop input 524 enter an empty to filler mode 526 or by receiving a new product selected input 528 enter a water plug mode 530. As mentioned above, the water plug mode 530 is optional since it is can be omitted for some product combinations, e.g. when switching from milk treatment to chocolate milk treatment.

After having received a timer lapse input 532 the processing system 100 enters a pre-production mode 534. If omitting the water plug mode 530 also the pre-production mode 534 can be omitted. In pre-production mode 534, when receiving a QT2 below GPT input 536 the processing system 100 may enter the fill to drain mode 514. Further, in some situations it may be beneficial to include the pre-sterilization mode or pre-production mode even if the water plug mode is omitted.

As illustrated, in the fill to reclaim mode 518 the system may enter fill to drain mode 514 after receiving a QT2 below RPT input 523.

In empty to filler mode 526, when receiving a QT2 below GPT input 538, the processing system 100 can enter an empty to reclaim mode 540. In the empty to reclaim mode 540, when receiving a QT2 below RPT input 542 the processing system 100 can enter an empty to drain mode 544.

In empty to drain mode 544, when receiving a timer lapse input 546, the processing system 100 can enter the idle mode 502.

Though the examples given herein refer to the food processing industry mainly, the general ideas are applicable to all sorts of processing systems handling more than one kind of product.

As described above, there is a need to be able to detect a transition from a first phase to a second phase in a processing system. This can be achieved by using two interrelated methods—a method for marking a change and a detecting a change as described below.

A method for marking a change from a first phase to a second phase in a processing system, said method comprising feeding a first product liquid having a first concentration level through a processing system, feeding a marker liquid having a marker concentration level through said processing system, and feeding a second product liquid having a second concentration level through said processing system, wherein said marker concentration level is lower than said first concentration level and said second concentration level.

The concentration levels can indicate amount of product compared to water.

An advantage is that the change from said first product liquid to said second product liquid can be detected although said first product liquid and said second product liquid have similar characteristics, e.g. conductivity properties.

A method for detecting a change from a first product to a second product in a processing system, said method comprising registering a first concentration level for a first product liquid by a sensor, registering a marker concentration level for said marker liquid by said sensor, registering a second concentration level for a second product liquid by said sensor, determining if said marker concentration level is lower than said first concentration level and said second concentration level is higher than said marker concentration level, and if so, outputting a detection signal indicating said change from said first product to said second product.

Correspondingly, a change from a first product to a second product can be achieved by using two interrelated apparatuses—an apparatus for marking a change and an apparatus for detecting a change as described below.

An apparatus for marking a change from a first phase to a second phase in a processing system, said apparatus comprising a control device configured to feed a first product liquid having a first concentration level through a processing system, feed a marker liquid having a marker concentration level through said processing system, and feed a second product liquid having a second concentration level through said processing system, wherein said marker concentration level is lower than said first concentration level and said second concentration level.

An apparatus for detecting a change from a first product to a second product in a processing system, said device comprising a concentration level sensor configured to register and output a first concentration level, a marker concentration level and a second concentration level, and a data processing device configured to receive said first concentration level, said marker concentration level and said second concentration level from said concentration level sensor, to determine if said marker concentration level is lower than said first concentration level and said second concentration level is higher than said marker concentration level, and if so, to output a detection signal indicating said change from said first product to said second product.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A processing system for a food product comprising:
   a plurality of storage tanks, each storage tank containing a different food product;
   a processing device configured to individually treat each of the different food products;
   a conduit for flushing the processing system;
   a processing line; and
   an apparatus configured to detect a transition from a first phase of a food product in the processing line to a second phase of the food product in the processing line, the apparatus including a first sensor configured to gather data indicating a product concentration of the food product at a first point in the processing line, a second sensor configured to gather data indicating a product concentration of the food product at a second point in the processing line, the second point being located downstream of the first point in the processing line, and a control device configured to receive a first data set from the first sensor and a second data set from the second sensor, the control device being configured to calibrate the second sensor by comparing the second data set with the first data set.

2. The processing system according to claim 1, further comprising a product recovery system and a residual product storage tank.

3. The processing system according to claim 1, wherein the food product from only one of the plurality of storage tanks is actively introduced into the processing line at a given time.

4. The processing system according to claim 3, wherein one of the food storage tanks stores a first food product and another food storage tank stores a second food product different from the first food product, and wherein a first fluid is introduced into the processing system through the conduit to flush out residues of the first food product in the processing system before introducing the second food product from the another storage tank.

* * * * *